(12) United States Patent
Ishikawa et al.

(10) Patent No.: US 9,434,880 B2
(45) Date of Patent: Sep. 6, 2016

(54) RADICAL INHIBITOR

(71) Applicants: IHI Corporation, Tokyo (JP); Yoshihiro Ishikawa, Tokyo (JP)

(72) Inventors: Yoshihiro Ishikawa, Tokyo (JP); Haruki Eguchi, Tokyo (JP)

(73) Assignees: IHI CORPORATION, Tokyo (JP); Yoshihiro Ishikawa, Tokyo (JP)

( * ) Notice: Subject to any disclaimer, the term of this patent is extended or adjusted under 35 U.S.C. 154(b) by 30 days.

(21) Appl. No.: 14/354,379

(22) PCT Filed: Sep. 27, 2012

(86) PCT No.: PCT/JP2012/074938
§ 371 (c)(1),
(2) Date: Apr. 25, 2014

(87) PCT Pub. No.: WO2013/061724
PCT Pub. Date: May 2, 2013

(65) Prior Publication Data
US 2014/0302604 A1 Oct. 9, 2014

(30) Foreign Application Priority Data

Oct. 27, 2011 (JP) ................. 2011-236486

(51) Int. Cl.
| | |
|---|---|
| *C09K 15/20* | (2006.01) |
| *C07C 225/14* | (2006.01) |
| *C07C 251/08* | (2006.01) |
| *C07C 251/10* | (2006.01) |
| *C09K 15/32* | (2006.01) |
| *C07D 211/58* | (2006.01) |
| *C07D 307/52* | (2006.01) |
| *C07F 15/02* | (2006.01) |
| *A61K 8/49* | (2006.01) |
| *A61Q 17/04* | (2006.01) |
| *C07D 307/58* | (2006.01) |

(52) U.S. Cl.
CPC ................. *C09K 15/20* (2013.01); *A61K 8/49* (2013.01); *A61Q 17/04* (2013.01); *C07C 225/14* (2013.01); *C07C 251/08* (2013.01); *C07C 251/10* (2013.01); *C07D 211/58* (2013.01); *C07D 307/52* (2013.01); *C07D 307/58* (2013.01); *C07F 15/025* (2013.01); *C09K 15/326* (2013.01); *A61K 2800/522* (2013.01)

(58) Field of Classification Search
CPC ... C09K 15/20; C09K 15/326; C07F 15/025; A61K 8/49; A61Q 17/04
USPC ....... 556/32, 34; 549/210; 435/375; 514/492
See application file for complete search history.

(56) References Cited

U.S. PATENT DOCUMENTS

| | | | |
|---|---|---|---|
| 3,975,382 A | 8/1976 | Avar et al. | |
| 4,008,225 A | 2/1977 | L'Eplattenier et al. | |
| 5,403,834 A | 4/1995 | Malfroy-Camine et al. | |
| 5,696,109 A | 12/1997 | Malfroy-Camine et al. | |
| 5,843,400 A | 12/1998 | Fujibayashi et al. | |
| 5,912,361 A | 6/1999 | Tsuchioka et al. | |
| 6,008,190 A | 12/1999 | Meade et al. | |
| 2005/0204486 A1 | 9/2005 | Sieber | |
| 2009/0035673 A1 | 2/2009 | Wu | |
| 2014/0011032 A1 | 1/2014 | Ishikawa | |
| 2014/0046021 A1 | 2/2014 | Ishikawa | |
| 2014/0235883 A1 | 8/2014 | Eguchi | |
| 2014/0323566 A1 | 10/2014 | Ishikawa | |

FOREIGN PATENT DOCUMENTS

| | | |
|---|---|---|
| EP | 0 726 077 A2 | 8/1996 |
| EP | 831836 A1 | 9/2000 |
| EP | 1513980 A1 | 3/2005 |
| EP | 2 657 223 A1 | 10/2013 |
| EP | 2 682 384 A1 | 1/2014 |
| EP | 2 733 713 A1 | 5/2014 |
| EP | 2 738 157 A1 | 6/2014 |
| JP | 3556690 B2 | 3/1995 |
| JP | 10-167787 A | 6/1998 |
| JP | 10-251263 A | 9/1998 |
| JP | 11-507646 A | 7/1999 |
| JP | 2002-153294 A | 5/2002 |
| JP | 2006-502313 A | 1/2006 |
| JP | 2009217088 A | 9/2009 |
| JP | 2011-153239 A | 8/2011 |
| WO | 94/13300 A1 | 6/1994 |
| WO | 96/18402 A1 | 6/1996 |
| WO | 96/40149 A1 | 12/1996 |
| WO | 03/035078 A1 | 5/2003 |
| WO | 03/104545 A1 | 12/2003 |

OTHER PUBLICATIONS

A. Mary Imelda Jayaseeli et al., [Iron(III)—salen] ion catalyzed H2O2 oxidation of organic sulfides and sulfoxides, Journal of Molecular Catalysis A: Chemical, May 15, 2009, vol. 309, pp. 103-110.

Annegret Hille et al., [N,N' -Bis (salicylidene)-1, 2-phenylenediamine] metal complexes with cell death promoting properties, JBIC Journal of Biological Inorganic Chmistry, Mar. 4, 2009, vol. 14, pp. 711-725.

International Search Report and Written Opinion of the ISA from corresponding International Application No. PCT/JP2012/074938 mailed Dec. 4, 2012.

Hiizu Iwamura "Design of Organic Ferromagnets" Feb. 1989, pp. 76-88.

Kristy Cochran et al. "cis-Diamminodichloronickel and Its Interaction With Guanine and Guanine-Cytosine Base Pair" vol. 13, No. 2, Apr. 2002, pp. 133-140.

(Continued)

*Primary Examiner* — Porfirio Nazario Gonzalez
(74) *Attorney, Agent, or Firm* — Brundidge & Stranger, P.C.

(57) ABSTRACT

A new radical inhibitor, a composition containing the new radical inhibitor, and a radical generation inhibition method using the new radical inhibitor are provided. A radical inhibitor according to the present invention contains a salen complex compound of a bivalent metal.

5 Claims, No Drawings

(56) References Cited

OTHER PUBLICATIONS

International Search Report from corresponding International Application No. PCT/JP2012/074938 mailed Dec. 4, 2012.
International Publication from corresponding International Application No. PCT/JP2012/074938 on May 2, 2013.
Yong Le, et al, Synthesis, Characterization, Antioxidative Activity and DNA Binding Properties of the Copper(II), Zinc (II), Nickel(II) Complexes with 1,2-Di(4'-iminonaringenin)ethane, College of Chemistry and Chemical Engineering and State Key Laboratory of Applied Organic Chemistry, vol. 56, No. 11, published Sep. 1, 2008, pp. 1528-1536.
Japanese Office Action dated Sep. 15, 2015.
Partial European Search Report dated Jul. 16, 2015 for European Patent Application 12844442.9.
Luiza N.H. Arakaki, et al., "Thermals Study of Chelates of Co(II), Cu(II), Ni(II), Cr(III), Mo(III), and Fe(III) with bis (Acetylacetone) Ehtylenediimine on Activated Silica Gel Surface", Journal of Thermal Analysis and Calorimetry, vol. 97(2009) 2, pp. 377-382.
Yong Sun, et al., "Toward understanding macrocycle specificity of iron on the dioxygen-binding ability: a theoretical study", PCCP, View Article Online/Journal Homepage/Table of Contents for this issue; Dynamic Article Links, Phys. Chem. Chem. Phys, 2011, vol. 13, pp. 13800-13808.
Xiu-Juan Qi, et al., "Anti-Spin-Delocalization Effect in Co—C Bond Dissociation Enthalpies", XP-002675419, Organometallics 2008 American Chemical Society, vol. 27, pp. 2688-2698.
Najat Aburas, et al., Electrochemical behavior and antioxidant activity of tetradentate Schiff bases and their copper(II) complexes, J Iran Chem Soc (2012), 9:859-864, DOI 10.1007/s13738-012-0I02-7; XP55200607A.
Takayuki Matsushita, et al., "A Facile Synthesis of Unsymmetrical Tetradentate SCHIFF-Base Ligands and Their Copper(II) and Nickel(II) Complexes", Polyhedron vol. 5, No. 3, pp. 735-738, 1986.
A.A. Osowole, et al., "Synthesis and Characterisation of Some Nickel(II) Synthesis and Reactivity in Inorganic and Metal-Organic Chemistry", β-Ketoamines and Their Adducts with 2, 2'-Bypyridine and 1, 10-Phenathroline, Synthesis and Reactivity in Inorganic and Metal-Organic Chemistry, 32:4, 783-799, DOI: 10.1081/SIM-120004446; http://dx.doi.org/10.1081/SIM-120004446.
Hong Ye Liu, et al., "An Initial Approach to Biologically Related Bridged Assemblies: Pyridinethiolate-Linked Fe4S4—Fe Complex Systems", Journal American Chemical Society 1991, vol. 113, pp. 9529-9539.
Yoshihiro Numata, et al., "Synthesis and Property of Nitrosyl Cobalt and Nitrosyl Iron Complexes with some Quadridentate Ligands", Inorganica Chimica Acta, vol. 43, 1980, pp. 193-197.
A.A. Osowole, et al., "Synthesis and Characterisation of Some Nickel(II) Synthesis and Reactivity in Inorganic and Metal-Organic Chemistry", β-Ketoarriines and Their Adducts with 2, 2'-Bypyridine and 1, 10-Phenanthroline, Synthesis and Reactivity in Inorganic and Metal-Organic Chemistry, 32:4, 2007, 783-799, DOI: 10.1081/SIM-120004446; http://dx.doi.org/10.1081/SIM-120004446.
A. Kotocova, et al., "Electrochemical Behaviour of a Series of Fe(III) Complexes with Tetradentate Schiff Base Ligands", Monatshefte für Chemie Chemical Monthly 125, Springer-Verlag 1994, pp. 491-495.
L. N. Smirnov, et al "Heat Stabilization of Poly(.epsilon.-caproamide)", Database Caplus [Online] Chemical Abstracts Service, Columbus, OH, Database Accession No. 1971:552364, May 13, 1971, 7 pages.
Eiichi Suenaga, "Ultraviolet Absorption Spectra of bis(3-hydroxy-2-pyridylmethylene)ethylenediamine", Nippon Kagaku Zasshi, vol. 81, 1960, pp. 1710-1713, Database Caplus [Online] Chemical Abstracts Service Columbus, OH, Database Accession No. 1962:5777.
Extended European Search Report (EESR) dated Jan. 20, 2016.

RADICAL INHIBITOR

TECHNICAL FIELD

The present invention relates to a radical inhibitor, a composition such as a cosmetic material containing the radical inhibitor, and a radical inhibition method using the radical inhibitor.

BACKGROUND ART

A "radical" means an atom, molecule, or ion that has unpaired electrons and is also called a free radical. Since radicals are normally highly responsive and have strong oxidation power, they react with any organic compounds such as carbohydrates, proteins, or fats.

It is well known that while products containing these organic compounds as their main components are preserved, they deteriorate due to generation of radicals, thereby generating offensive smell, causing discoloration or color degradation, hardening, decomposition, denaturation, or hypofunction. Furthermore, radicals and peroxides produced by chemical reactions linked to the generation of the radicals have injurious effects on cells and tissues, so that they are recently considered as one of main causes of the development or growth of various diseases such as skin aging, adult diseases, inflammatory diseases, or malignant neoplasms.

Since the radicals are easily generated under daily environmental conditions such as lighting and heating, deterioration of products and adverse effects on humans due to the radicals and peroxides which are reaction products of the radicals may happen in wide fields such as a food field, a cosmetic field, a medical field, and a chemical industrial product field. Therefore, to inhibit generation of radicals is important in wide fields without limitation to a certain field in terms of product quality, preservation of functions, and maintenance of human health.

The currently most used means in each field for solving this problem is to mix a substance generally called a radical scavenger, that is, a substance that reacts to radicals and prevents or inhibits responsiveness of the radicals, in a product or its raw materials. However, the radical scavenger is disadvantageous in that the radical inhibiting effect by the radical scavenger does not continue for a long period of time. Under such circumstances, there is a demand for further development of materials that have excellent functionality and a radical generation inhibiting effect.

On the other hand, U.S. Pat. No. 3,556,690 discloses a carboxylated derivative, which has a carboxyl group obtained by oxidizing a hydroxymethyl group and/or a hemiacetal hydroxyl group of carbohydrate, and a method for producing the carboxylated derivative. Furthermore, Japanese Patent Application Laid-Open (Kokai) Publication No. 10-251263 and Japanese Patent Application Laid-Open (Kokai) Publication No. 2002-153294 disclose trehalose oxide (α-D-glucopyranosyl-α-D-glucopyranoside) obtained by oxidizing two hydroxymethyl groups of α,α-trehalose (α-D-glucopyranosyl-α-D-glucopyranoside).

Furthermore, a review article about an organic magnetic substance is introduced in "Molecular Design Aimed at Organic Ferromagnetic Substances" by Hiizu Iwamura, February 1989 issue, p.p. 76-88 and this review describes that a magnet is produced with polymeric materials by means of synthesis of "high-spin molecules" having more parallel spins than those of conventional metallic magnetic substances. However, this literature does not mention that the relevant drug itself will be magnetized.

Furthermore, "Structural Chemistry" by Kristy Cochran et al., 13 (2002), p.p. 133-140 introduces a technique that replaces platinum contained in cisplatin with another element; however, this literature does not mention that the relevant drug itself will be magnetized.

CITATION LIST

Patent Literature

[Patent Literature 1] U.S. Pat. No. 3,556,690
[Patent Literature 2] Japanese Patent Application Laid-Open (Kokai) Publication No. 10-251263
[Patent Literature 3] Japanese Patent Application Laid-Open (Kokai) Publication No. 2002-153294
[Non Patent Literature 1] Hiizu Iwamura, "Molecular Design Aimed at Organic Ferromagnetic Substances," February 1989 issue, p.p. 76-88
[Non Patent Literature 2] Kristy Cochran et al., Structural Chemistry, 13 (2002), p.p. 133-140

SUMMARY OF INVENTION

Problems to be Solved by the Invention

It is an object of the present invention to provide a new radical inhibitor, a composition such as a cosmetic material containing the new radical inhibitor, and a radical inhibition method using the new radical inhibitor.

Means for Solving the Problems

As a result of earnest examination, the inventor of the present invention has found that a metal complex compound of a bivalent metal has a notable radical inhibiting action, thereby devising the invention of this application.

Specifically speaking, a first invention of the present application is a radical inhibitor containing a bivalent metal complex compound as a radical inhibiting component. Free radicals such as active enzymes are trapped by a bivalent metal such as a bivalent metal coordinated by salen.

Furthermore, a second invention of the present application is various compositions, for example, external use compositions such as cosmetic materials, medical compositions, and food compositions, that contain a bivalent metal complex compound as an accessory component in order to prevent the progress of, for example, denaturation or decay caused by radicals. The content of the bivalent metal complex in the relevant composition is an amount that is necessary and sufficient to exert an inhibiting effect on the radicals. Preferably, a metal-salen complex compound such as iron and hydrated crystal neotrehalose (Hayashibara Biochemical Labs., Inc.), which is a kind of oligosaccharide as a mixture component should be mixed at a weight ratio of, for example, 3-5:7-5.

Furthermore, a third invention of the present application is a radical generation inhibition method using a bivalent metal complex compound.

A preferred embodiment of the metal complex compound is represented by the following formula (I).

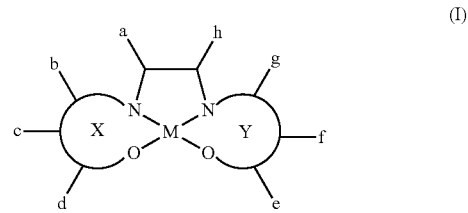

Each of X and Y is a five-membered ring structure including a coordinate bond between N and M, or its six-membered ring structure, wherein M is a bivalent metallic element composed of Fe (iron), Cr (chromium), Mn (manganese), Co (cobalt), Ni (nickel), Mo (molybdenum), Ru (rubidium), Rh (rhodium), Pd (palladium), W (tungsten), Re (rhenium), Os (osmium), Ir (iridium), Pt (platinum), Nd (niobium), Sm (samarium), Eu (europium) or Gd (gadolinium). If both X and Y are the five-membered ring structure, b and g do not exist and Formula (I) is any one of (i) to (iv).

(i) Each of a to h is hydrogen or any one of (A) to (G) mentioned below and —C(=O)m (where m is hydrogen or any one of (A) to (G) mentioned below);

(ii) each of (c, d) and (f, e) forms part of a heterocyclic structure and constitutes a condensate of the compound represented by Formula (I) and the heterocyclic structure, each of a, b, g, and h is hydrogen or any one of (A) to (G) mentioned below and —C(=O)m (where m is hydrogen or any one of (A) to (G) mentioned below), the heterocyclic structure is any one of three-membered to seven-membered ring structures containing furan, theophene, pyrrole, pyrrolidine, pyrazole, pyrazolone, imidazole, 2-isoimidazole, oxazole, isoxazole, thiazole, imidazole, imidazolidine, oxazoline, oxazolidine, 1,2-pyran, thiazine, pyridine, pyridazine, pyrimidine, pyrazine, orthoxadine, oxazine, piperidine, piperazine, triazine, dioxane, or morpholine, and a side chain for the heterocyclic structure is halogen, —R, —O—R (where R is one functional group selected from a hydrocarbon group including a methyl group), or hydrogen;

(iii) each of (c, d) and (f, e) forms part of one of condensed ring structures containing benzene or naphthalene and anthracene and forms a condensate of the compound represented by Formula (I) and the condensed ring structure, each of a, b, g, and h is hydrogen or any one of (A) to (G) mentioned below, and a side chain for the condensed ring structure is halogen, R—O—: (where R is one functional group selected from a hydrocarbon group including a methyl group), or hydrogen;

(iv) each of a and h forms part of a cyclic hydrocarbon structure containing a compound mentioned below and forms a condensate of the compound represented by Formula (I) and the cyclic hydrocarbon structure

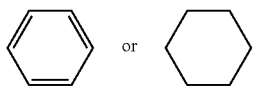 [SMILES: c1ccccc1 ; C1CCCCC1]

b to g and a side chain for the cyclic hydrocarbon structure is hydrogen or any one of (A) to (G) mentioned below.

(A) —$CO_2R$, —C(=O)R (where R represents hydrogen or chain or cyclic hydrocarbon having a saturated structure with carbon number 1 to 6 (C1 to C6) or an unsaturated structure (alkane or alkyne))

(B) —CO(OCH$_2$CH$_2$)$_2$OCH$_3$ (C) 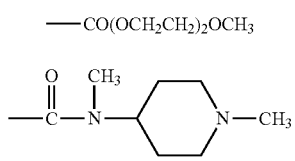

(D) 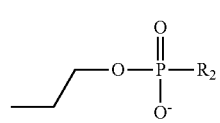

(where $R_2$ represents one of nucleic acids which are formed of adenine, guanine, thymine, cytosine, or uracil, or a plurality of the nucleic acids which are combined together);

(E) —NHCOH or —$NR_1R_2$ (where $R_1$ and $R_2$ represent hydrogen or chain or cyclic hydrocarbon with the same or different saturated structure with carbon number 1 to 6 or unsaturated structure (alkane or alkyne));

(F) —$NHR_3$—, —$NHCOR_3$, —$CO_2$—$R_3$, —S—S—$R_3$ or —$R_3$ (where $R_3$ represents hydrogen or a substituted compound condensed as a result of elimination of a leaving group such as a hydroxyl group; and the substituted compound is functional molecules including at least one of enzymes, antibodies, antigens, peptides, amino acids, oligonucleotides, proteins, nucleic acids, and medical molecules); and (G) halogen atoms such as chlorine, bromine, or fluorine.

A metal-salen complex among metal complexes according to the present invention is a compound in which salen (N,N'-bis(2-hydroxybenzylidene)ethylene diamine) is coordinated to metal atoms. The applicant of this application revealed that the metal-salen complex compound as a metal complex compound itself is magnetic without containing a magnetic carrier and has an anticancer effect (International Publication No. 2010/058280). A substituted compound described in that publication can be used as $R_3$ mentioned above. The content of the publication constitutes descriptions of the specification of this application. A skeleton of the metal complex compound relative to, for example, medical molecules provides a means for protecting the medical molecules against free radicals by being added to a composition such as the medical molecules or binding to the medical molecules.

Advantageous Effects of Invention

A new radical inhibitor, a composition containing the new radical inhibitor, and a radical inhibition method using the new radical inhibitor can be provided according to the present invention as explained above.

DESCRIPTION OF EMBODIMENTS

An embodiment of the metal complex compound represented by the aforementioned formula (I) is any one of the following formulas (II) to (XI).

(II)
X, Y: six-membered ring structure
(a to h)=H

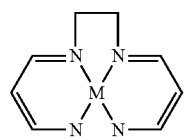

(III)
X, Y: six-membered ring structure
(c, f)=C(O)H
(a, b, d, e, g, h)=H

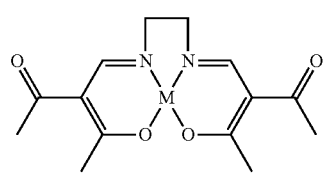

(IV)
X, Y: five-membered ring structure, (a, c, d, e, f, h)=H

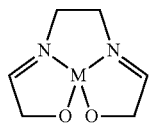

(V)
X, Y: six-membered ring structure
(a, b, g, h): H
(e, f), (c, d): constitute part of furan and furan is condensed with a main skeleton.
M: Fe

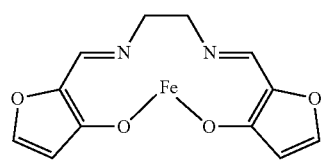

(VI)
X, Y: six-membered ring structure
(a, h): constitute part of cyclohexane and cyclohexane is condensed with a main skeleton.
(c, d), (e, f): constitute benzene
(b, g): H
M: Fe

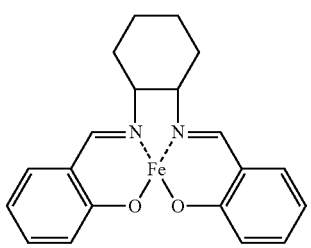

(VII)
X, Y: six-membered ring structure
(a, h): constitute part of benzene
(c, d), (e, f): constitute benzene
(b, g): H
M: Fe

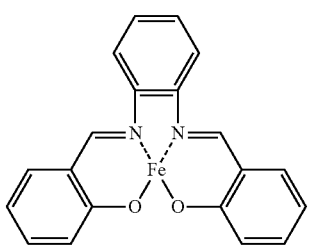

(VIII)
X, Y: six-membered ring structure
(c, d), (e, f): constitute anthracene
(a, b, g, h): H
M: Fe

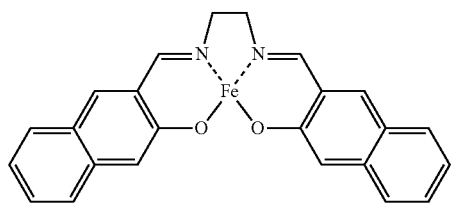

(IX)
X, Y: six-membered ring structure
(c, d), (e, f): constitute anthracene
(a, b, g, h)=H
Isomer of (V)
M: Fe

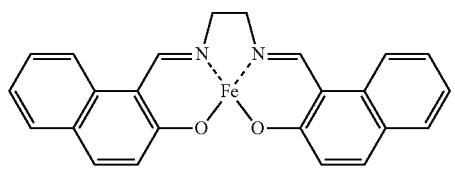

(X)
X, Y: six-membered ring structure
(c, d), (e, f): constitute benzene
Side chains at meta positions of benzene are halogens (bromine).
(a, b, g, h): H
M: Fe

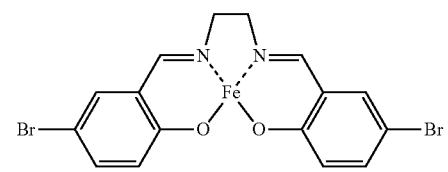

(XI)
X, Y: six-membered ring structure
(c, d), (e, f): constitute benzene
Side chains at meta positions of benzene are methoxyl groups.
(a, b, g, h): H
M: Fe

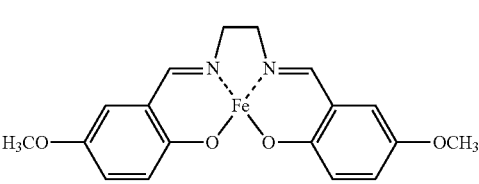

EXAMPLE

Next, examples of the present invention will be explained.

Example 1

Synthesis of Metal Complex Compound (II)

First Synthesis Example

The metal complex compound (II) was synthesized in accordance with the following reaction formulas.

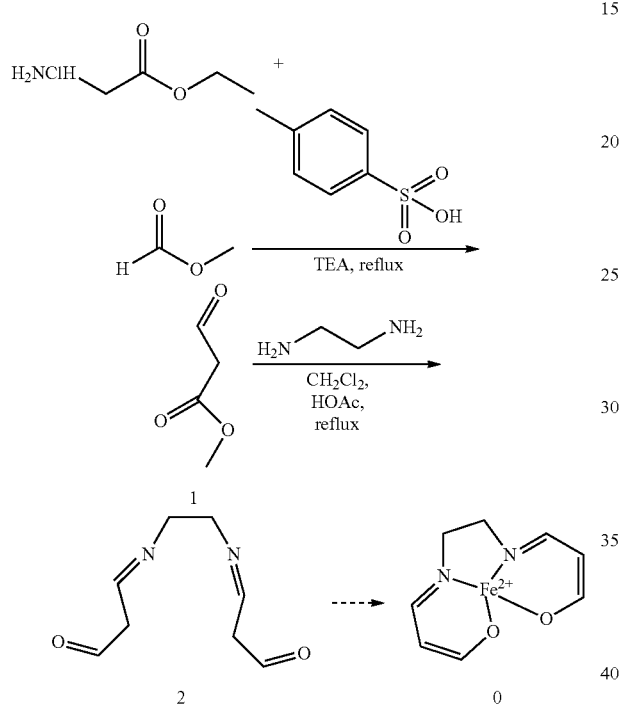

P-TsOH (10 mg) was added to an ethyl formate solution (60 ml) containing glycine methyl ester monohydrochloride (10.0 g, 0.079 mol). The obtained solution was heated to boiling. Several drops of triethylamine were put into the solution while being boiled; and the mixed solution was brought to reflux for 24 hours and then cooled down to room temperature. Subsequently, white triethylaminehydrochloride was filtered. The residue was concentrated to 20 ml. The obtained solution was cooled down to a temperature of −5 degrees Celsius and then filtered. A reddish brown concentrated solution which was a residue (Compound 1) was obtained.

Synthesis of Compound 2

$CH_2Cl_2$ (20 ml) was dissolved in Compound 1. Then, ethane-1,2-diamine (1.2 g) and acetic acid (HOAc) (20 μl) were added to the obtained solution; and this reacted mixed solution was then brought to reflux for 6 hours. Subsequently, the reactant mixed solution was cooled down to room temperature, thereby obtaining 4 g of a yellow oil concentrate (Compound 2). Purity of the obtained Compound 2 was enhanced by flash column chromatography by using silica gel.

Synthesis of Compound 0

Compound 2 and triethylamine were introduced in methanol (50 ml) and a solution of metallic chloride ($FeCl_3(4H_2O)$ when synthesizing an iron-salen complex compound) was mixed in methanol (10 ml) in a nitrogen atmosphere. The mixture components were mixed for one hour in a nitrogen atmosphere, thereby obtaining a brown compound. Then, this compound was dried in a vacuum, the obtained compound was diluted with dichloromethane (400 ml), washed twice with a saline solution, was dried over $Na_2SO_4$, and then dried in a vacuum, thereby obtaining Compound 0 (the metal-salen complex compound (II)).

Second Synthesis Example

The metal complex compound (II) was synthesized in accordance with the following reaction formulas.

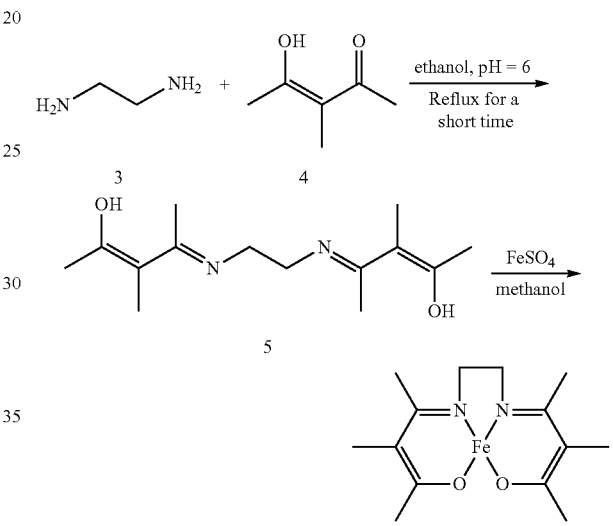

Compound 5 was synthesized by introducing 3.4 g of 3-methylacetylacetone (Compound 4) and 0.9 g of ethylene diamine (Compound 3) into anhydrous methanol (50 ml) while adjusting pH to pH 6 by using acetic acid on ice. The obtained solution was brought to reflux for 15 minutes and allowed to evaporate until its volume reduces to one half its original volume. Then, water of the same volume was added to the solution and let it deposit, thereby obtaining 1.4 g of white compound (Compound 5).

Subsequently, Compound 5 (1.2 g, 5 mmol) was introduced into methanol (50 ml) and $FeSO_4 \cdot 7H_2O$ (1.4 g, 5 mmol) was added to the obtained solution, thereby obtaining a pale bluish green solution. As this mixed solution was stirred for 8 hours at room temperature in a nitrogen atmosphere, its color gradually changed to brown. Subsequently, the solution was allowed to evaporate to reduce a half of its volume and then the same volume of water was added to the obtained solution. Next, vacuum was produced to allow methanol to evaporate, thereby obtaining brown lumps. These lumps were gathered, washed with water, and dried by producing a vacuum, thereby obtaining 360 mg of the target compound (the metal-salen complex compound (II)).

Third Synthesis Example

The metal complex compound (II) was synthesized in accordance with the following reaction formulas.

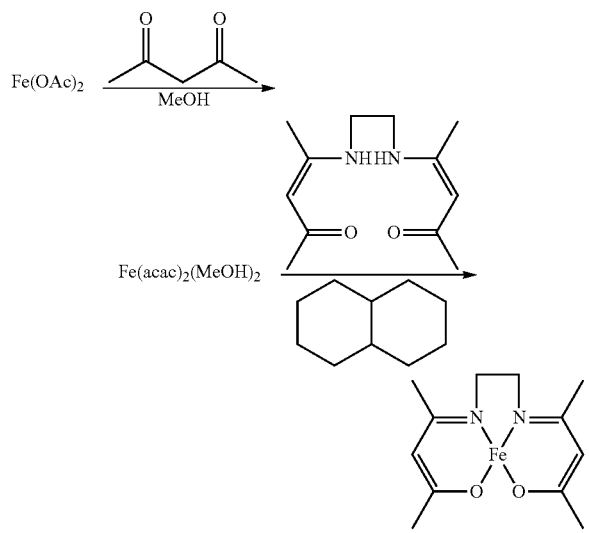

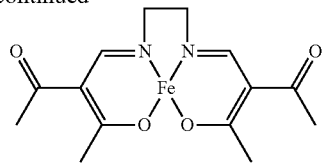

Iron (II) acetate (0.78 g, 4.5 mmol) and degassed methanol (20 ml) were introduced into a reaction container in a nitrogen atmosphere and acetylacetone (0.91 g, 9.9 mmol) was added to the obtained solution. The solution was stirred in a reflux for 15 minutes and then let it stand to cool. Deposited crystals were filtered, and the obtained solution was washed with cooled methanol (10 ml). Subsequently, the solution was dried under reduced pressure, thereby obtaining 0.58 g (yield 67%) of an intermediate.

The intermediate (240 mg, 0.75 mmol), ligand atoms (210 mg, 0.75 mmol), and degassed decalin (10 ml) were introduced into a reaction container in a nitrogen atmosphere and the obtained solution was stirred in a reflux for 30 minutes. After letting the solution stand to cool and filtering a deposited solid, the obtained solid was washed with degassed cyclohexane (3 ml). Next, the solution was dried under reduced pressure, thereby obtaining 101 mg of a product (the metal complex compound (III)).

Iron (II) acetate (0.83 g, 4.8 mmol) and degassed methanol (48 ml) were introduced into a reaction container in a nitrogen atmosphere and acetylacetone (0.95 g, 9.5 mmol) was added to the obtained solution. The solution was stirred in a reflux for 15 minutes and then let it stand to cool. Deposited crystals were filtered and the obtained solution was washed with cooled methanol (10 ml). Subsequently, the solution was dried under reduced pressure, thereby obtaining 1.07 g of an intermediate.

The intermediate (1.07 g, 3.4 mmol), ligand atoms (0.7 g, 3.4 mmol), and degassed decalin (30 ml) were introduced into a reaction container in a nitrogen atmosphere and the obtained solution was stirred in a reflux for 1 hour. After letting the solution stand to cool and filtering a deposited solid, the obtained solid was washed with degassed cyclohexane (10 ml). Next, the solution was dried under reduced pressure, thereby obtaining 0.17 g of a product (iron complex compound (II)).

Example 2

Synthesis of Metal Complex Compound (III)

The metal complex compound (III) was synthesized in accordance with the following reaction formulas

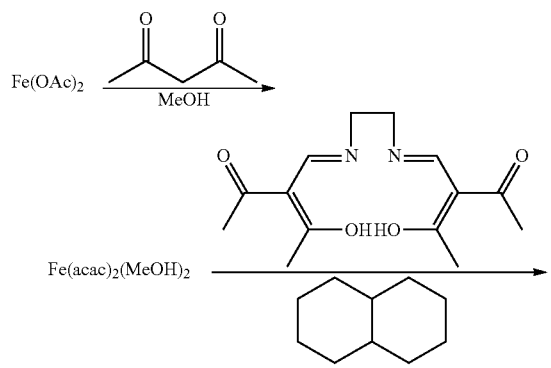

Example 3

Synthesis of Metal Complex Compound (IV)

The metal complex compound (IV) was synthesized in accordance with the following reaction formulas

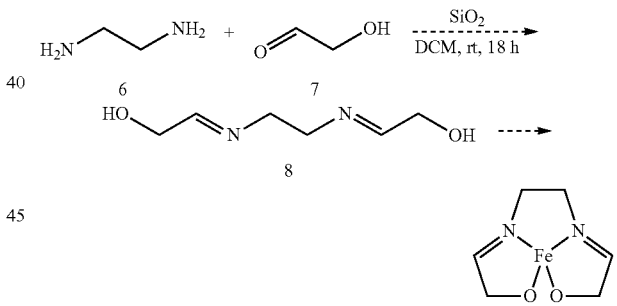

Iron (II) acetate (0.83 g, 4.8 mmol) and degassed methanol (48 ml) were introduced into a reaction container in a nitrogen atmosphere and acetylacetone (0.95 g, 9.5 mmol) was added to the obtained solution. The solution was stirred in a reflux for 15 minutes and then let it stand to cool. Next, Compound 7 (120 mg, 2.0 mmol) and SiO$_2$ (1 g) were added to a solution of Compound 6 (60 mg, 1.0 mmol) dissolved in CH$_2$Cl$_2$ (10 ml); and the obtained solution was stirred all night at room temperature to cause a reaction, thereby synthesizing Compound 8. Subsequently, the obtained Compound 8 together with iron (II) acetate (0.83 g, 4.8 mmol) and degassed methanol (48 ml) was introduced into a reaction container in a nitrogen atmosphere and acetylacetone (0.95 g, 9.5 mmol) was added to the obtained solution. The solution was stirred for 15 minutes in a reflux and deposited crystals were filtered, thereby obtaining a brown target compound (the metal complex compound (IV)).

Example 4

The compounds (V) to (XI) were synthesized by a method described on pages 43 to 47 of International Publication No. 2010/058280. Bromine or a methoxyl group which is a side chain is added to a main skeleton, when forming a metal complex bond to salen, by substituting a protecting group (NHBoc), which is bonded to a benzene ring at a para position with an OH group of the benzene ring, with bromine or the methoxyl group. With the compounds (VIII) and (IX) in which (c, d) and (e, f) constitute anthracene, the following compound is used as a starting material instead of para-nitrophenol.

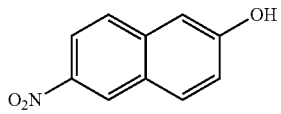 [SMILES: O=[N+]([O-])c1ccc2cc(O)ccc2c1]

Regarding synthesis of the metal-salen complex (VI) in which (a, h) constitute cyclohexane and the metal-salen complex (VII) in which (a, h) constitute benzene, the target salen before forming a coordinate bond with a metal is produced by a method described in Journal of Thermal Analysis and calorimetry, Vol. 75 (2004) 599-606, Experimental on page 600.

Example 5

A compound represented by the following formula (1) is a salen complex compound of bivalent iron. This compound binds to active enzymes existing in cancer cells and traps enzyme radicals, so that the iron changes from bivalent to trivalent. In this example, how the compound represented by the following formula (1) traps the enzyme radicals generated from the cancer cells was checked by using hematoxylin which produces color when it detects a trivalent complex.

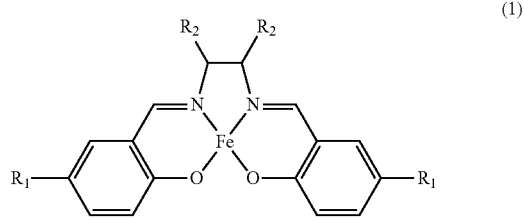

(1)

(Each of $R_1$, $R_2$, $R_3$, and $R_4$ is "H.")

Firstly, melanoma cells (clone M3) which are skin cancer were cultivated where the iron-salen complex compound (concentration: 1 mM) represented by the above-mentioned formula (1) exists. A circular petri dish was used for the cultivation, a round button-shaped magnet (diameter: 10 mm) with 240 mT magnetic flux density was placed under the petri dish (diameter: 100 mm), and that petri dish was cultivated for 24 hours (a culture medium was PBS (phosphate buffered saline); cultivation time: 24 hours; and cultivation temperature: 37° C.). This culture medium was stained with hematoxylin.

A staining method is as follows:
(1) perform deparaffinization, remove xylene, and rinse the culture medium with water;
(2) perform nuclear staining with hematoxylin for 5 to 15 minutes;
(3) rinse it with water lightly;
(4) separate it with 0.25% to 0.5% aqueous hydrochloric acid as necessary;
(5) rinse it with running water for 10 minutes (or 15 minutes in winter) to be stained;
(6) rinse it with water for 5 minutes (this is necessary when saddening was performed by using alkali water);
(7) perform cytoplasmic staining (eosin) for 1 to 10 minutes; and
(8) perform dehydration, penetration, and inclusion, thereby terminating staining.

As a result, it was confirmed that the culture medium was stained in bluish-purple under and around the button-shaped magnet. This shows that the compound (represented by the formula (1)) changed from bivalent to trivalent by trapping enzyme radical atoms produced from the cancer cells. It was also confirmed by using the microscope that the melanoma cells were dead in the stained area. It should be noted that the existence of the button-shaped magnet is not indispensable for the bivalent metal salen complex to exert an anti-radical action. The button-shaped magnet was placed in order to increase the concentration of the bivalent metal salen complex.

The invention claimed is:

1. A radical inhibitor comprising a metal complex compound of a bivalent metal as a radical inhibiting component,
   wherein the metal complex compound is represented by a following formula (I):

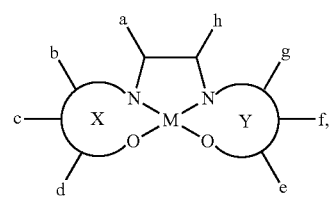

wherein at least one of a-h is hydrogen or methyl group,
wherein M is a bivalent metallic element composed of Fe, Co, Ru, Rh, Os, or Ir, and
wherein each of X and Y is a six-membered ring structure.

2. The radical inhibitor of claim 1, wherein each of b-g is hydrogen.

3. The radical inhibitor of claim 1, wherein each of b-g is methyl group.

4. The radical inhibitor of claim 1, wherein each of b, d, e, and g is methyl group.

5. A radical inhibitor containing a complex compound of a bivalent metal as a radical inhibiting component,
   wherein the complex compound being useful for utilization of magnetism of the complex compound without using magnetic support made from magnetic bodies,
   wherein structure of the complex compound comprises structure of N, N'-ethylenebis (acetylacetoneiminate) metal, wherein the metal is a bivalent metallic element.

* * * * *